United States Patent [19]

Stanco et al.

[11] Patent Number: 4,614,190

[45] Date of Patent: Sep. 30, 1986

[54] PHOTORADIATION METHOD AND ARRANGEMENT

[76] Inventors: Alexei Stanco, 75A Angos Street, Adelaide, Australia, 5000; James A. Piper, Macquarie Uni., North Ryde, Sydney, New South Wales, Australia, 2113

[21] Appl. No.: 495,354

[22] PCT Filed: Sep. 8, 1982

[86] PCT No.: PCT/AU82/00151

§ 371 Date: May 9, 1983

§ 102(e) Date: May 9, 1983

[87] PCT Pub. No.: WO83/00811

PCT Pub. Date: Mar. 17, 1983

[30] Foreign Application Priority Data

Sep. 8, 1981 [AU] Australia ............................... PF0657

[51] Int. Cl.[4] .............................................. A61N 5/00
[52] U.S. Cl. .................................................... 128/395
[58] Field of Search ...................... 128/303.1, 395-398

[56] References Cited

U.S. PATENT DOCUMENTS

| | | | |
|---|---|---|---|
| 3,900,034 | 8/1975 | Katz et al. | 128/395 |
| 3,914,013 | 10/1975 | Rosenberg | 128/303 X |
| 4,266,549 | 5/1981 | Kimura | 128/303.1 |
| 4,309,998 | 1/1982 | Aron et al. | 128/303.1 |
| 4,336,809 | 6/1982 | Clark | 128/303.1 X |
| 4,391,275 | 7/1983 | Frankhauser et al. | 128/303.1 |

FOREIGN PATENT DOCUMENTS 581941 11/1977 U.S.S.R. ........................... 128/303.1

OTHER PUBLICATIONS

Anders et al, "Investigation . . . Dye Lasers", Conf: Laser 77 Opto-Elec., Munich, Ger., Jun. 1977, pp. 520–526.
Dougherty et al, "Photoradiation Therapy for the Treatment of Malignant Tumors", Cancer Research, vol. 38, pp. 2628–2635, Aug. 1978.

*Primary Examiner*—Lee S. Cohen
*Attorney, Agent, or Firm*—Steele, Gould & Fried

[57] ABSTRACT

A method and arrangement for activating a photoirradiable chemical such as hematoporphyrin derivative (HPD) particularly in vivo by use of pulsed radiation of the required frequency higher energy input with less damage surrounding tissue can be achieved.

5 Claims, No Drawings

PHOTORADIATION METHOD AND ARRANGEMENT

BACKGROUND OF THE INVENTION

This invention relates to an arrangement for effecting photoirradiation and to a method of photoirradiation for the activation of chemical substances.

It is known that selective drugs such as hematoporphyrin derivative (HPD) when administered to the animal body firstly can be selectively retained in tumours and cancerous tissue and can by effective photoirradiation be made to effect by means which are not yet totally clear, an affect which has a deleterious effect upon the tumour or cancerous tissues.

It is to be realised that while hematoporphyrin derivative is referred to in this specification it is in fact a mixture of compounds and the use of this invention may extend to particular photosensitive elements included within the compound referred to as hematoporphyrin derivative.

Similarly it can extend to other chemical compounds having a similar deleterious effect on tumours or cancerous tissue.

This invention accordingly relates firstly to a method effecting a more effective activation for this purpose of a drug of this type or the invention relates to the apparatus incorporating the particular parts and characteristics necessary to make the discovery effective or the invention relates to the treatment of the human body or the invention relates to the treatment of any animal body.

Thus far, there has been experienced difficulties in providing irradiation of a selected location with sufficient intensity to ensure sufficient activation of the chemical to effect a sufficient action to have the desired effect on the tumour or cancerous tissue without the irradiation itself unduly affecting by heating or otherwise the surrounding flesh.

In the considerable research that has been thus far conducted, there has been difficulty in achieving a sufficiently high irradiation by using a conventional source of radiation without causing this undue damage elsewhere.

SUMMARY OF THE INVENTION

The invention will be better understood when referred to specific illustrations but in general terms according to this invention there is proposed that instead of activating or irradiating the chemical for the purpose described from a continuous source, there is proposed that the source is pulsed so that while individual pulses of the radiation energy have a high energy state, none the less, the average energy and therefore the general heating of tissue will be somewhat less than would be necessary for a continuous source providing such high energy excitation continuously.

The effect is to thereby cause the excitation and hence expected cytotoxic effect while the chemical, particularly hematoporphyrin derivative (HPD), is being held within the tumour in the body.

Accordingly the invention in one form can be said to reside in a method of preparation of an active compound in vivo comprising the steps of administering a photosensitive chemical and irradiating the photosensitive chemical in situ with pulsed electromagnetic radiation to prepare the active compound.

In one preferred form of the invention the wave length of the electromagnetic radiation is in the range of from 626 nanometers to 636 nanometers.

In a further preferred form the pulse length of the electromagnetic radiation is from twenty nanoseconds to fifty nanoseconds and the pulse frequency is selected from the range of from one hundred hertz to ten kilohertz.

As indicated above in a preferred form of the invention the photosensitive chemical may be hematoporphyrin derivative.

In one preferred form of the invention the electromagnetic radiation may be supplied by a gold vapour laser.

In an alternative form of the invention the active compound is of a type useful for the treatment of tumours and cancerous tissue.

In an alternative form the invention is said to reside in activation of a photosensitive chemical comprising the steps of irradiating the photosensitive chemical with radiant energy as a pulsed supply, such that the energy supplied has a multiple number of short pulses of high energy, but at the same time, has a much lower average energy rate.

In a preferred form of this aspect of the invention the high energy radiation is in the order of tens of kilowatts and the average energy rate is in the order of several watts.

In a further preferred form of the invention the invention may be said to reside in a gold vapour laser adapted for the treatment of tumours or cancerous tissue, the laser adapted to emit high intensity light at a wave length of 627.8 nanometers at a pulse length of from twenty to fifty nanoseconds and a frequency of from one hundred hertz to ten kilohertz.

A discussion of a specific example of this arrangement may be of assistance in fully understanding the implications of this invention and its application in respect of apparatus appropriate for this application, the method of treating a photosensitive chemical and finally the method of treatment of either a human body or of an animal body or the selective destruction of tumours within the human or animal body.

DETAILED DESCRIPTION OF THE PREFERRED EMBODIMENTS

It is known that irradiation of tumours and particularly malignant tumours within the human body following administration of the specific drug hematoporphyrin derivative with intensive light and in the wave length range of 626 to 636 nanometers can reduce and in some cases totally destroy the tumour cells.

This specificity of the irradiation range relates both to the sensitivity of the chemical and to the selective transparency of skin and tissue in the human or animal body.

Instant powers of irradiation up to three hundred milliwatts per square centimeter have been found necessary to achieve activation sufficient to effect an adequate cytotoxic effect.

The discovery by this invention has been that by using a pulsed gold vapour laser that this can provide high energy pulses in the order of tens of kilowatts during short repetitive pulses this being directly in a wave length of 627.8 nanometers which is the transition wave length of the neutral gold atom.

With a pulse rate of approximately ten kilohertz and a pulse length of from twenty to fifty nanoseconds average power of several watts can be obtained at conversion efficiencies on the electrical input energy typically 0.3%.

Accordingly in this particular instance there is the dual advantage that while the overall output has an average energy level similar to other supplies, none the less, the very high energy pulses will give an accentuated effect with respect to activation of the photosensitive chemical drug while not having unduly high average powers effecting general deterioration of the surrounding tissues by general heating and other effects.

It is of general value that a gold vapour laser is a device which has a compact structure, is relatively straight forward to operate and can give a low divergent beam suitable for coupling into an optical fibre delivery system which is considered most important and useful in delivering any beam into a suitable location within a human or animal body.

While reference has been made to the gold vapour laser it is not intended that the invention should necessarily be limited to this. In its broadest concept it relates to the concept of pulsing the activating irradiation and as such can relate to all of the generally radiating sources.

These can be for instance pulsed dye lasers where these are pumped by way of a flash lamp, for example, xenon or a crystal laser or gas discharge laser or an excimer laser.

Typical of continuous wave lasers which can also be pulsed are a krypton ion laser, argon ion pumped dye laser or perhaps in the future hollow cathode metal vapour lasers. Even sources such as a conventional filament lamp source with appropriate filtering, an arc lamp source with appropriate filtering or even a pulsed xenon flash lamp with appropriate filtering could be used.

What is claimed is:

1. A method for treating living tissue, wherein the tissue contains an administered hematoporphyrin derivative for sensitizing the tissue to irradiation treatment, the method comprising the step of irradiating the tissue with pulsed electromagnetic energy from a laser having a wave length in the range of 626 to 636 nanometers, the energy having a power level with a peak value on the order of tens of kilowatts, but an average value only on the order of several watts, the peak value being sufficient to activate the hematoporphyrin derivative, but too small to effect general deterioration of surrounding tissue.

2. A method according to claim 1, wherein the electromagnetic radiation has a pulse length in the range of 20 to 50 nanoseconds.

3. A method according to claims 1 or 2, wherein the pulse frequency is in the range of 100 hertz to 10 kilohertz.

4. A method according to claim 1, comprising the step of emitting the electromagnetic energy from a gold vapor laser.

5. A method according to claim 1, further comprising the step of coupling the electromagnetic energy emitted from the laser into at least one optical fiber for delivery of the energy to a tissue treatment site.

* * * * *